US00PP22871P2

(12) United States Plant Patent
Sakazaki

(10) Patent No.: US PP22,871 P2
(45) Date of Patent: Jul. 24, 2012

(54) ***MECARDONIA* PLANT NAMED 'USMECA8205'**

(50) Latin Name: *Mecardonia hybrida*
Varietal Denomination: USMECA8205

(75) Inventor: Ushio Sakazaki, Shiga (JP)

(73) Assignee: Plant 21 LLC, Bonsall, CA (US)

( * ) Notice: Subject to any disclaimer, the term of this patent is extended or adjusted under 35 U.S.C. 154(b) by 193 days.

(21) Appl. No.: 12/802,247

(22) Filed: Jun. 1, 2010

(51) Int. Cl.
*A01H 5/00* (2006.01)

(52) U.S. Cl. ..... Plt./263.1

(58) Field of Classification Search ..... Plt./263.1
See application file for complete search history.

*Primary Examiner* — Annette Para
(74) *Attorney, Agent, or Firm* — C. A. Whealy

(57) ABSTRACT

A new and distinct cultivar of *Mecardonia* plant named 'USMECA8205', characterized by its low mounding to trailing plant habit; freely branching habit; dense and bushy growth habit; early and freely flowering habit; bright yellow-colored flowers; and good garden performance.

1 Drawing Sheet

Botanical designation: *Mecardonia hybrida.*
Cultivar denomination: 'USMECA8205'.

BACKGROUND OF THE INVENTION

The present invention relates to a new and distinct cultivar of *Mecardonia* plant, botanically known as *Mecardonia hybrida*, and hereinafter referred to by the name 'USMECA8205'.

The new *Mecardonia* plant is a product of a planned breeding program conducted by the Inventor in Higashiomi, Shiga, Japan and Bonsall, Calif. The objective of the breeding program is to create new freely branching *Mecardonia* plants with numerous flowers.

The new *Mecardonia* plant originated from a cross-pollination made by the Inventor on Apr. 20, 2007 in Higashiomi, Shiga, Japan of a proprietary seedling selection of *Mecardonia hybrida* identified as code number 06M53, not patented, as the female, or seed, parent with a proprietary seedling selection of *Mecardonia hybrida* identified as code number 06M54, not patented, as the male, or seed, parent. The new *Mecardonia* plant was discovered and selected by the Inventor as a single flowering plant from within the progeny of the stated cross-pollination in a controlled greenhouse environment in Bonsall, Calif. on May 21, 2008.

Asexual reproduction of the new *Mecardonia* plant by vegetative tip cuttings in a controlled environment in Bonsall, Calif. since Jul. 23, 2008, has shown that the unique features of this new *Mecardonia* plant are stable and reproduced true to type in successive generations.

SUMMARY OF THE INVENTION

Plants of the new *Mecardonia* have not been observed under all possible environmental conditions. The phenotype may vary somewhat with variations in environment such as temperature and light intensity, without, however, any variance in genotype.

The following traits have been repeatedly observed and are determined to be the unique characteristics of 'USMECA8205'. These characteristics in combination distinguish 'USMECA8205' as a new and distinct cultivar of *Mecardonia* plant:

1. Low mounding to trailing plant habit.
2. Freely branching habit; dense and bushy growth habit.
3. Early and freely flowering habit.
4. Bright yellow-colored flowers.
5. Good garden performance.

Plants of the new *Mecardonia* differ from plants of the female parent selection in the following characteristics:

1. Plants of the new *Mecardonia* are more mounding than and not as creeping as plants of the female parent selection.
2. Plants of the new *Mecardonia* flower earlier than plants of the female parent selection.
3. Plants of the new *Mecardonia* have smaller flowers than plants of the female parent selection.

Plants of the new *Mecardonia* differ from plants of the male parent selection in the following characteristics:

1. Plants of the new *Mecardonia* are more mounding than and not as compact as plants of the male parent selection.
2. Plants of the new *Mecardonia* flower earlier than plants of the male parent selection.
3. Plants of the new *Mecardonia* have larger flowers than plants of the male parent selection.

Plants of the new *Mecardonia* can be compared to plants of *Mecardonia* 'USMECA67', disclosed in U.S. Plant Pat. No. 15,777. In side-by-side comparisons conducted in Bonsall, Calif., plants of the new *Mecardonia* differed from plants of 'USMECA67' in the following characteristics:

1. Plants of the new *Mecardonia* were more mounding than and not as creeping as plants of 'USMECA67'.
2. Plants of the new *Mecardonia* flowered earlier than plants of 'USMECA67'.
3. Plants of the new *Mecardonia* had smaller flowers than plants of 'USMECA67'.

Plants of the new *Mecardonia* can also be compared to plants of *Mecardonia* 'Sunmecareki', disclosed in U.S. Plant Pat. No. 18,210. In side-by-side comparisons conducted in Bonsall, Calif., plants of the new *Mecardonia* differed from plants of 'Sunmecareki' in the following characteristics:

1. Plants of the new *Mecardonia* were more mounding than and not as creeping as plants of 'Sunmecareki'.
2. Plants of the new *Mecardonia* flowered earlier than plants of 'Sunmecareki'.
3. Plants of the new *Mecardonia* had smaller flowers than plants of 'Sunmecareki'.

BRIEF DESCRIPTION OF THE PHOTOGRAPHS

The accompanying photographs illustrate the overall appearance of the new *Mecardonia* plant. These photographs show the colors as true as it is reasonably possible to obtain in colored reproductions of this type. Colors in the photographs may differ slightly from the color values cited in the detailed botanical description which accurately describe the colors of the new *Mecardonia* plant.

The photograph at the bottom of the sheet comprises a side perspective view of a typical flowering plant of 'USMECA8205' grown in a container.

The photograph at the top of the sheet is a close-up view of a typical flowering plant of 'USMECA8205'.

DETAILED BOTANICAL DESCRIPTION

The aforementioned photographs and following observations, measurements and values describe plants grown during the early spring in an outdoor nursery in Bonsall, Calif. During the production of the plants, day temperatures ranged from 18° to 24° C., night temperatures ranged from 5° to 8° C. and light levels ranged from 7,000 to 10,000 foot-candles. Plants were pinched one time and were eight weeks old when the description and photographs were taken. In the following description, color references are made to The Royal Horticultural Society Colour Chart, 2007 Edition, except where general terms of ordinary dictionary significance are used.

Botanical classification: *Mecardonia hybrida* 'USMECA8205'.

Parentage:

*Female, or seed, parent*.—Proprietary seedling selection of *Mecardonia hybrida* identified as code number 06M53, not patented.

*Male, or pollen, parent*.—Proprietary seedling selection of *Mecardonia hybrida* identified as code number 06M54, not patented.

Propagation:

*Type*.—By vegetative tip cuttings.

*Time to initiate roots, summer*.—About three days at temperatures ranging from 17° C. to 29° C.

*Time to initiate roots, winter*.—About five days at temperatures ranging from 17° C. to 21° C.

*Time to produce a rooted plant, summer*.—About 19 days at temperatures ranging from 17° C. to 29° C.

*Time to produce a rooted plant, winter*.—About 23 days at temperatures ranging from 17° C. to 21° C.

*Root description*.—Medium in thickness, fibrous; white in color.

*Rooting habit*.—Freely branching; moderately dense.

Plant description:

*Plant form/growth habit*.—Low mounding to trailing plant habit; vigorous growth habit.

*Plant height*.—About 8 cm.

*Plant diameter or spread*.—About 38 cm.

*Lateral branches*.—Quantity per plant: Freely branching habit with numerous lateral branches developing per plant; pinching enhances lateral branch development; dense and bushy growth habit. Length: About 19 cm. Diameter: About 1.5 mm. Internode length: About 1.5 cm to 2.5 cm. Texture: Smooth, glabrous. Strength: Moderately strong. Orientation: Initially upright then falling over and become trailing. Color: Close to 146C.

Foliage description:

*Arrangement*.—Opposite, simple.

*Length*.—About 1.7 cm.

*Width*.—About 1 cm.

*Shape*.—Elliptical.

*Apex*.—Acute.

*Base*.—Attenuate.

*Margin*.—Serrate.

*Texture, upper and lower surfaces*.—Smooth, glabrous.

*Venation pattern*.—Pinnate.

*Color*.—Developing leaves, upper surface: Close to 137A. Developing leaves, lower surface: Close to 146B. Fully expanded leaves, upper surface: Close to 137A; venation, close to 137B. Fully expanded leaves, lower surface: Close to 147B; venation, close to 147B.

*Petioles*.—Length: About 3 mm. Diameter: About 1 mm. Texture, upper and lower surfaces: Smooth, glabrous. Color, upper and lower surfaces: Close to 137D.

Flower description:

*Flower arrangement and habit*.—Solitary axially flowers that face mostly upward to outwardly; freely flowering habit with about 300 open flowers per plant at one time.

*Natural flowering season*.—Early flowering habit; plants begin flowering about four weeks after planting; long flowering period, spring until late autumn in California; flowering continuous during this period.

*Flower longevity on the plant*.—About five days; flowers persistent.

*Fragrance*.—None detected.

*Flower diameter*.—About 1.2 cm by 1.5 cm.

*Flower depth* (*height*).—About 1.3 cm.

*Flower buds*.—Length: About 1 cm. Diameter: About 4 mm. Shape: Obovate. Color: Close to 11A.

*Corolla*.—Arrangement: Single whorl of four petals; petals fused at the base. Petal length, upper petal: About 9 mm. Petal length, lateral petals: About 1 cm. Petal length, lower petal: About 8 mm Petal width, upper petal: About 8 mm. Petal width, lateral petals: About 6 mm. Petal width, lower petal: About 6 mm. Petal shape, all petals: Cordate to obovate. Petal apex, all petals: Rounded to emarginate. Petal margin, all petals: Entire. Petal texture, upper and lower surfaces, all petals: Smooth, glabrous; upper petal with tiny hairs at petal base. Color: All petals, when opening, upper surface: Close to 11A. All petals, when opening, lower surface: Close to 8B. Upper petal, fully opened, upper surface: Close to 11A; towards the base, close to 145C; longitudinal streaks, close to N199A to N199B. Lateral and lower petals, fully opened, upper surface: Close to 11A; towards the base, close to 145C; color does not fade with development. All petals, fully opened, lower surface: Close to 8B; color does not fade with development.

*Sepals*.—Quantity per flower: Two. Length: About 6 mm. Width: About 1.5 mm. Shape: Lanceolate. Apex: Acute. Base: Truncate. Margin: Entire. Texture, upper and lower surfaces: Smooth, glabrous. Color, upper and lower surfaces: Close to 144A.

*Flower bracts*.—Quantity per flower: Three. Length: About 6 mm. Width: About 3 mm. Shape: Elliptical. Apex: Acute. Base: Truncate. Margin: Entire. Texture, upper and lower surfaces: Smooth, glabrous. Color, upper and lower surfaces: Close to 144A.

*Peduncles*.—Length: About 5 cm. Diameter: About 1 mm. Aspect: About 30° to 45° from stem axis. Strength: Moderately strong; wiry. Texture: Smooth, glabrous. Color: Close to 145A.

*Reproductive organs*.—Stamens: Quantity per flower: Four. Filament length: About 3 mm. Filament color: Close to 145C. Anther shape: Oval, bi-lobed. Anther length: About 1 mm. Anther color: Close to 155D. Pollen amount: Scarce. Pollen color: Close to 155D. Pistils: Quantity per flower: One. Pistil length: About 3 mm. Style length: About 1.5 mm. Style color: Close to 144D. Stigma shape: Oval. Stigma color: Close to 144C. Ovary color: Close to 144C. Seed/fruit: Seed and fruit production has not been observed.

Disease/pest resistance: Plants of the new *Mecardonia* have not been shown to be resistant to pathogens and pests common to *Mecardonia* plants.

Temperature tolerance: Plants of the new *Mecardonia* have been observed to tolerate temperatures ranging from about 1° C. to about 46° C.

It is claimed:

1. A new and distinct *Mecardonia* plant named 'USMECA8205' as illustrated and described.

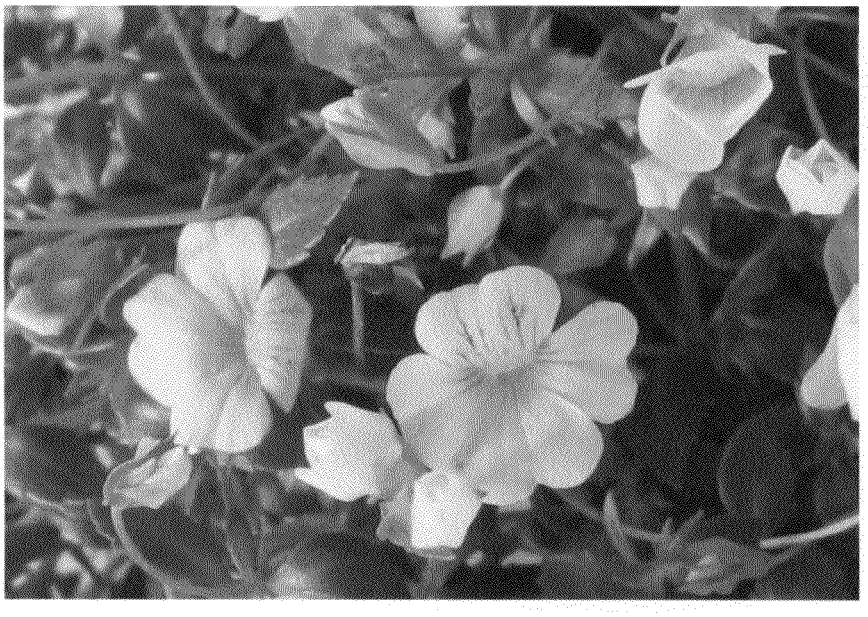
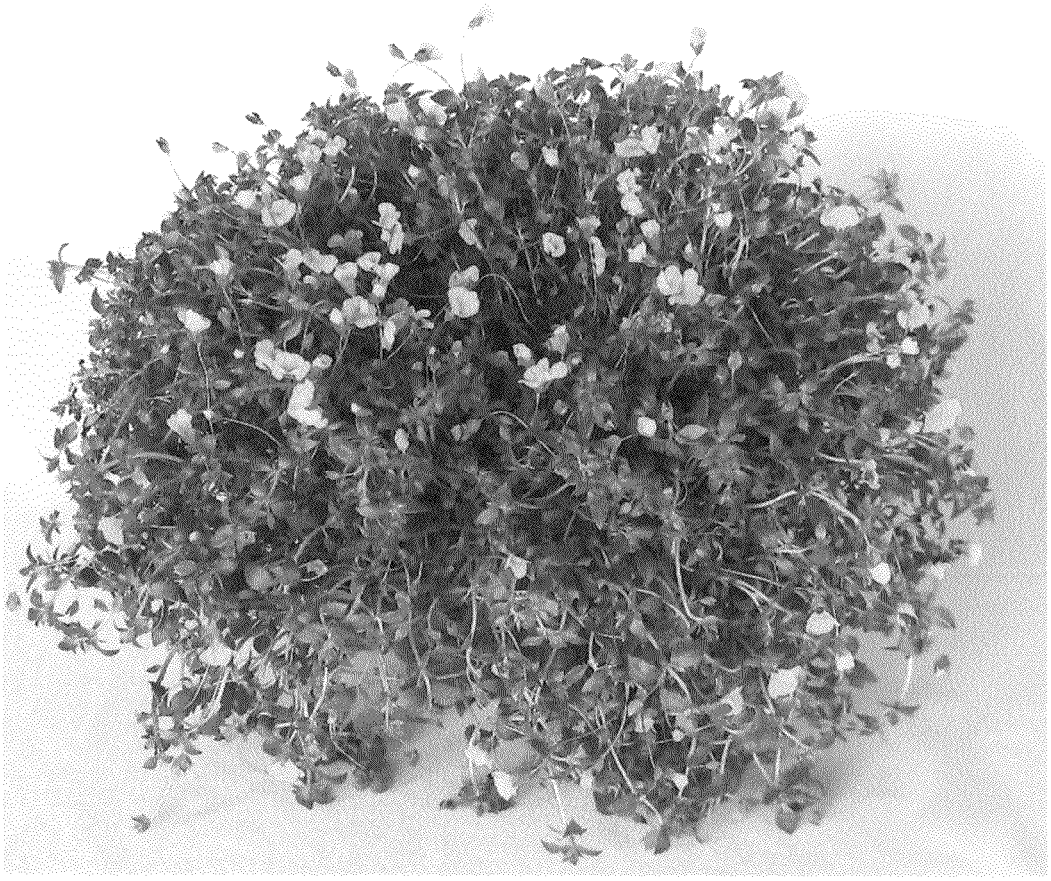

* * * * *